United States Patent [19]

Meguro et al.

[11] Patent Number: 4,775,687
[45] Date of Patent: Oct. 4, 1988

[54] THIAZOLIDINE DERIVATIVES, THEIR PRODUCTION AND USE

[75] Inventors: Kanji Meguro, Nishinomiya; Takeshi Fujita, Takarazuka, both of Japan

[73] Assignee: Takeda Chemical Industries, Ltd., Osaka, Japan

[21] Appl. No.: 869,704

[22] Filed: Jun. 2, 1986

[30] Foreign Application Priority Data

Jun. 10, 1985 [JP] Japan .................. 60-126626

[51] Int. Cl.$^4$ .................. C07D 417/12; A61K 31/425
[52] U.S. Cl. .................. 514/369; 548/180; 548/183
[58] Field of Search .................. 548/183, 180; 514/369

[56] References Cited

U.S. PATENT DOCUMENTS

| | | | |
|---|---|---|---|
| 4,287,200 | 9/1981 | Kawamatsu et al. | 548/183 |
| 4,340,605 | 7/1982 | Kawamatsu et al. | 548/183 |
| 4,461,902 | 7/1984 | Kawamatsu et al. | 548/183 |
| 4,572,912 | 2/1986 | Yoshioka | 548/183 |

FOREIGN PATENT DOCUMENTS 177353 4/1986 European Pat. Off. ............ 548/183

OTHER PUBLICATIONS

Sohda et al., Chem. Pharm. Bull., 30(10), 3563-3573, 3580-3600, (1982).
Fujita et al., Diabetes, vol. 32, 804-810, (1983).
Sohda et al., Chem. Pharm. Bull., 32(6), 2267-2278, (1984).

Primary Examiner—Robert Gerstl
Attorney, Agent, or Firm—Wenderoth, Lind & Ponack

[57] ABSTRACT

A thiazolidinedione derivative of the general formula:

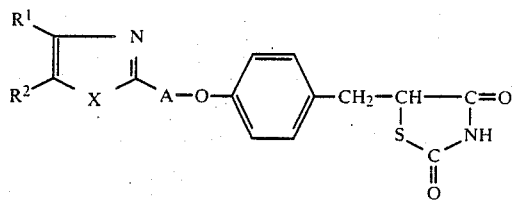

wherein X is an oxygen or sulfur atom, $R^1$ and $R^2$ each independently is hydrogen or a hydrocarbon residue which may optionally be substituted and $R^1$ and $R^2$ may jointly, together with the oxazole or thiazole ring, form a condensed ring and A is a lower alkylene group; or a salt thereof, are novel compounds, which exhibit in mammals blood sugar- and lipid-lowering activity, and are of value as a therapeutic agent for diabetes and/or therapeutic agent for hyperlipemia.

9 Claims, No Drawings

THIAZOLIDINE DERIVATIVES, THEIR PRODUCTION AND USE

This invention relates to novel thiazolidinedione derivatives having blood sugar and lipid lowering activity, methods of producing the same and antidiabetic agents containing the same.

Various biguanide type compounds and sulfonylurea type compounds have so far been used as antidiabetic agents. However, biguanides are rather obsolete nowadays because they induce lactic acidosis. Sulfonylureas, on the other hand, have potent blood sugar lowering activity but frequently cause severe hypoglycemia, so that much care is necessary in using them. Accordingly, the appearance of novel type antidiabetics free of these drawbacks has been waited for. Meanwhile, Japanese Patent Publications Kokai No. 22636/80 and Kokai No. 64586/80, Chemical & Pharmaceutical Bulletin, vol. 30, p. 3563 (1982), ibid., vol. 30, p. 3580 (1982) and ibid., vol. 32, p. 2267 (1984) describe that various thiazolidinedione derivatives exhibit blood sugar and lipid lowering activity. Antidiabetic activity of ciglitazone was also reported in Diabetes, 32, P. 804 (1983). None of them, however, has not come into practical use as an antidiabetic agent mainly because they are (1) weak in effect and/or (2) high in toxicity.

The present inventors synthesized and evaluated various compounds not specifically described in the above-cited patent publications and, as a result, compounds having potent pharmacological activity with low toxicity were found.

It is an object of the invention to provide those compounds which have a wide safety margin between the pharmacologically effective dose and the dose at which toxicity and/or adverse effects may appear and therefore can be put to practical use as antidiabetics.

The present invention thus provides:

(1) Thiazolidinedione derivatives of the general formula:

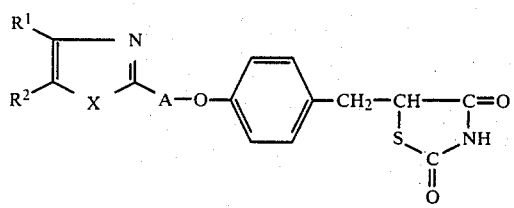

wherein X is an oxygen or sulfur atom, $R^1$ and $R^2$ each independently hydrogen or a hydrocarbon residue which may optionally be substituted and $R^1$ and $R^2$ may jointly, together with the oxazole or thiazole ring, form a condensed ring and A is a lower alkylene group, and salts thereof;

(2) Pharmaceutical compositions suitable for the therapy of a mammal suffering from diabetes and/or hyperlipemia, which contain as the effective component a thiazolidinedione derivative of the general formula (I) or a pharmacologially acceptable salt thereof.

(3) A method of producing thiazolidinedione derivatives of the general formula (I) and salts thereof which comprises hydrolyzing a compound of the general formula:

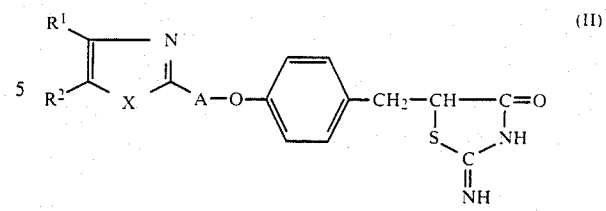

wherein the symbols are as defined above, or a salt thereof; and (4) A method of producing thiazolidinedione derivatives of the general formula:

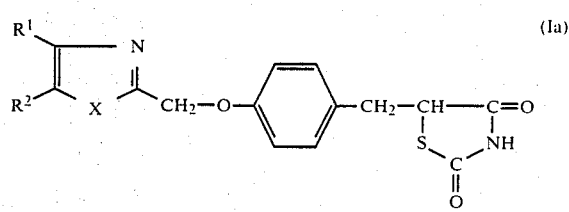

wherein the symbols are as defined above, and salts thereof, which comprises reacting a compound of the general formula:

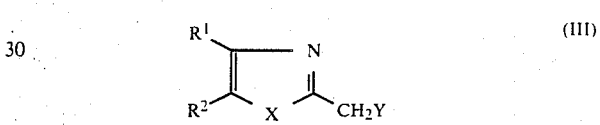

wherein $R^1$, $R^2$ and X are as defined above and Y is a halogen atom, with a compound of the formula:

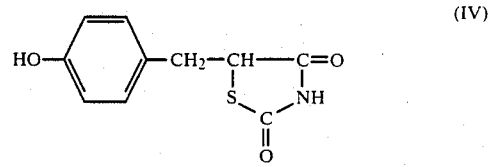

The hydrocarbon residue represented by $R^1$ and/or $R^2$ in the above general formulas (I), (Ia), (II) and (III) may be an aliphatic hydrocarbon residue, an alicyclic hydrocarbon residue, an alicyclic-aliphatic hydrocarbon residue, an aromatic-aliphatic hydrocarbon residue or an aromatic hydrocarbon residue. Said aliphatic hydrocarbon residue includes saturated aliphatic hydrocarbon residues containing 1-8 carbon atoms, (e.g. methyl, ethyl, propyl, isopropyl, butyl, isobutyl, sec-butyl, t-butyl, pentyl, hexyl, heptyl and octyl), preferably 1-4 carbon atoms; said alicyclic hydrocarbon residue includes saturated alicyclic hydrocarbon residues containing 3-7 carbon atoms, such as cyclopropyl, cyclobutyl, cyclopentyl, cyclohexyl and cycloheptyl, and unsaturated alicyclic hydrocarbon residues containing 5-7 carbon atoms, such as 1-cyclopentenyl, 2-cyclopentenyl, 3-cyclopentenyl, 1-cyclohexenyl, 2-cyclohexenyl, 3-cyclohexenyl, 1-cycloheptenyl and 2-cycloheptenyl; said alicyclic-aliphatic hdyrocarbon residue includes groups resulting from bonding the abovementioned alicyclic hydrocarbon residues to the abovementioned aliphatic hydrocarbon residues and containing 4-9 carbon atoms, such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, cycloheptylmethyl and cycloheptylethyl; said aromatic-aliphatic hydrocarbon residue includes phenylalkyl groups containing 7-9 carbon atoms, such as benzyl, phenethyl, 1-phenylethyl and phenylpropyl, and naphthylalkyl groups containing 11-13 carbon atoms, such as α-naphthylmethyl, α-naphthylethyl and β-naphthylethyl; and said aromatic hydrocarbon residue includes, among others, phenyl and naphthyl (α-naphthyl, β-naphthyl). By saying that $R^1$ and $R^2$ jointly, together with the oxazole or thiazole ring, form a condensed ring, it is precisely meant that $R^1$ and $R^2$, together with the thiazole or oxazole ring carbon atoms to which they are attaching, form a ring. Thus, it is meant that $R^1$ and $R^2$ are combined together to form a saturated or unsaturated divalent chain hydrocarbon residue containing 3-5 carbon atoms. Examples of said chain hydrocarbon residue are $-CH_2CH_2CH_2-$, $-CH_2CH_2CH_2CH_2-$, $-CH_2CH_2CH_2CH_2CH_2-$, $-CH=CHCH_2-$, $-CH=CH-CH=CH-$, $-CH=CH-CH=CH-CH_2-$ and $-CH=CH-CH_2CH_2-$.

The hydrocarbon residue represented by $R^1$ and/or $R^2$ may have at least one substituent in any position thereof. When $R^1$ and/or $R^2$ contains an alicyclic group, $R^1$ and/or $R^2$ may have, on the ring thereof, 1-3 lower alkyl groups containing 1-3 carbon atoms (e.g. methyl, ethyl, propyl, isopropyl). When $R^1$ and/or $R^2$ contains an aromatic hydrocarbon residue or when $R^1$ and $R^2$ combinedly form a condensed ring, the ring may be substituted with 1-4 substituents, which may be the same or different. Said substituents include, among others, halogen (fluorine, chlorine, iodine), hydroxy, cyano, trifluoromethyl, lower alkoxy (e.g. one containing 1-4 carbon atoms, such as methoxy, ethoxy, propoxy or butoxy), lower alkyl (e.g. one containing 1-4 carbon atoms, such as methyl, ethyl, propyl, isopropyl or butyl) and lower alkylthio (e.g. one containing 1-3 carbon atoms, such as methylthio, ethylthio, porpylthio or isopropylthio).

A lower alkylene groups represented by A is a straight or branched chain having 1 to 3 carbon atoms and includes methylene, ethylene, propylene and trimethylene.

The halogen represented by Y in formula (III) includes chlorine, bromine and iodine.

Compounds of the general formula (I) can form salts with bases since they have an acidic nitrogen atom in their thiazolidine ring. Such salts include, among others, pharmacologically acceptable salts such as sodium, potassium, magnesium and calcium salts.

The compounds (I) and salts thereof according to the invention exhibit excellent blood sugar and blood lipid lowering activities in mammals (e.g mouse, rat, dog, cat, monkey, horse, human) and are low in acute toxicity as well as in sabacute toxicity. Therefore, the thiazolidinedione derivatives (I) and salts thereof are useful in the treatment of hyperlipidemia and/or diabetes and complications resulting therefrom. They are generally administered orally in the form of tablets, capsules, powders or granules, for instance. In some instances, they may be administered parenterally in the form of injections, suppositories or pellets, among others. In using them as therapeutic agents for diabetes or hyperlipidemia, they can be administered generally in an oral daily dose of 0.01-10 mg/kg or a parenteral daily dose of 0.005-10 mg/kg. Desirably, they are administered in such dose every day or intermittently 2-4 times a week.

The compounds of general formula (I) or salts thereof can be produced by hydrolyzing the compounds of general formula (II) or salts thereof. This hydrolysis reaction is generally carried out in an appropriate solvent in the presence of water and a mineral acid. Examples of the solvent which are generally used are alkanols (e.g. methanol, ethanol, propanol, 2-propanol, butanol, isobutanol, 2-methoxyethanol), dimethyl sulfoxide, sulfolane, dioxane and dimethoxyethane. The mineral acid is, for example, hydrochloric acid, hydrobromic acid or sulfuric acid and is used in an amount of 0.1-10 moles, preferably 0.2-3 moles, per mole of the compound of general formula (II). Water is used generally in large molar excess relative to the compound of general formula (II). This reaction is generally carried out with warming or heating and the reaction temperature is generally 60°-150° C. The heating time is generally several hours to ten and odd hours.

Those compounds of general formula (I) wherein A is methylene and salts thereof, namely the compounds of general formula (Ia) and salts thereof [hereinafter collectively referred to as "compounds (Ia)"], can be obtained by reacting a compound of general formula (III) with a compound of general formula (IV) or a salt thereof [hereinafter collectively referred to as "compound (IV)"]. The reaction of the compound of general formula (III) and the compound (IV) is generally carried out in the presence of an appropriate solvent and an appropriate base and this reaction gives the compounds (Ia).

Such solvent includes, among others, dimethylformamide, dimethyl sulfoxide, sulfolane, tetrahydrofuran and dimethoxyethane. Examples of said base are sodium hydride, potassium hydride, sodium amide, sodium alkoxide (e.g. sodium methoxide, sodium ethoxide), potassium alkoxide (e.g. potassium t-butoxide) and potassium carbonate. This reaction is preferably carried out by first allowing formation of a dianion by bringing such base into contact with the compound (IV) in a molar ratio of 2:1 and thereafter adding the compound of general formula (III) in an amount of 1 mole per mole of compound (IV). This condensation reaction is carried out generally at 0°-120° C., preferably 20°-100° C., and the reaction time is generally 0.5-5 hours.

The thus-produced thiazolidinedione derivatives (I) and salts thereof can be isolated and purified by known separation/purification techniques such as, for example, concentration, concentration under reduced pressure, solvent extraction, crystallization, recrystallization, phase transfer and chromatography.

The starting compounds (II) can be produced, for example, by the following methods:

(1) The process illustrated below gives those compounds of general formula (I) wherein X is an oxygen atom, namely the compounds of general formula (IIa), and salts thereof [hereinafter collectively referred to as "compounds (IIa)].

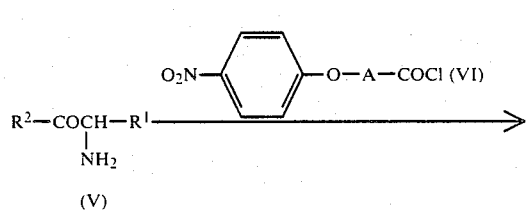

-continued

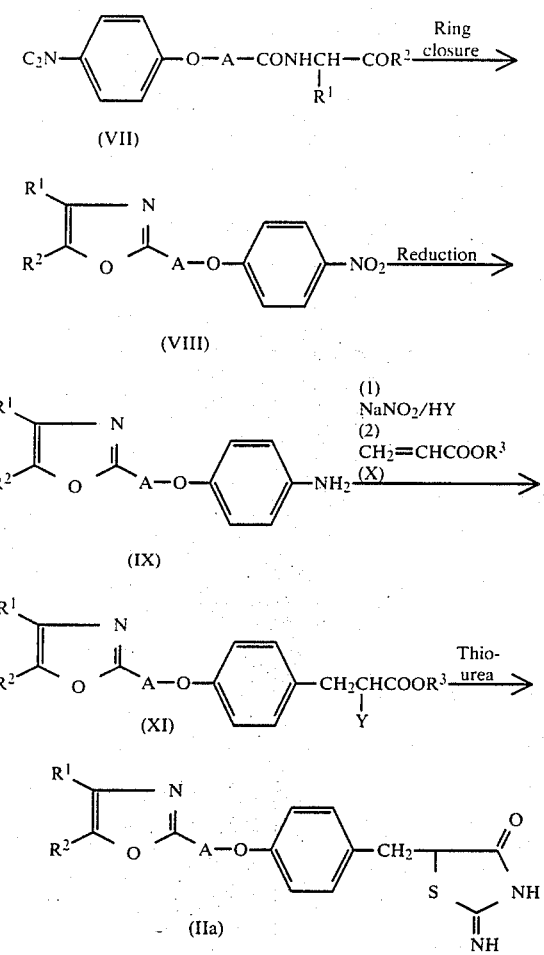

[In the above formulas, $R^1$, $R^2$ and A are as defined above and $R^3$ is hydrogen or a lower alkyl group.]

The reaction for deriving the compound (VII) from the compound (V) is carried out in the manner of condensation of the compound (V) with the compound (VI) in the presence of a deacidifying agent (e.g. potassium carbonate, sodium carbonate, sodium hydrogen carbonate, potassium hydrogen carbonate, sodium hydroxide, potassium hydroxide, triethylamine). This reaction can be conducted in a solvent, such as dimethylformamide, dimethyl sulfoxide, tetrahydrofuran, ethyl ether, ethyl acetate, chloroform or dichloromethane, or a mixed solvent prepared by adding water to such solvent as necessary, at $-10°$ C. to $50°$ C.

The compound (VII) is then subjected to ring closure, whereby the compound (VIII) can be derived. This reaction is carried out generally in the presence of a dehydrating agent. Known dehydrating agents, such as phosphorus oxychloride, thionyl chloride, phosphorus pentoxide, polyphosphoric acid, polyphosphoric acid esters, acetic anhydride and sulfuric acid, and mixtures of these, may suitably be used. Although the reaction conditions may vary depending on the dehydrating agent employed, this reaction can be effected generally in an inert solvent (e.g. benzene, toluene, xylene, dichloromethane, chloroform) at about $30°-140°$ C., or in an excess of the dehydrating agent, which serves also as a solvent, within said temperature range. The dehydrating agent is used in an amount of 1–30 moles per mole of compound (VII).

The reaction for deriving the compound (IX) from the compound (VIII) can be readily carried out in the manner of a conventional catalytic reduction using palladium-on-carbon as catalyst or a conventional reduction using zinc or iron in combination with acetic acid. The compound (IX) may be isolated in pure form or may be subjected to the next reaction step without isolation or purification.

The reaction for deriving the compound (XI) from the compound (IX) is carried out in the manner of the so-called Meerwein arylation. Thus, the compound (IX) is diazotized in the presence of a hydrohalogenic acid (HY) and then reacted with acrylic acid or an ester thereof (X) in the presence of a copper catalyst (e.g. cuprous oxide, cupric oxide, cuprous chloride, cupric chloride, cuprous bromide, cupric bromide). The compound (IX) may be purified, for example by chromatography or may be submitted to the next reaction step without isolation and purification.

Reaction of the compound (XI) with thiourea then gives (IIa). This reaction is carried out generally in a solvent such as an alcohol (e.g. methanol, ethanol, propanol, 2-propanol, butanol, isobutanol, 2-methoxyethanol), dimethylformamide, dimethyl sulfoxide or sulfolane. The reaction temperature is generally $20°-180°$ C., preferably $60°-150°$ C. Thiourea is used in an amount of 1–2 moles per mole of compound (XI). In this reaction, a hydrogen halide is formed as a byproduct with the progress of the reaction, whereby the hydrohalogenic acid salt of compound (IIa) is formed. In this case, the reaction may be carried out in the presence of sodium acetate, potassium acetate or the like so that the hydrogen halide can be captured thereby and (IIa) can be produced in the free form. Such acid acceptor is used generally in an amount of 1–1.5 moles per mole of compound (XI). Such reaction gives the compound (IIa), which may be isolated as desired or may be submitted directly to the next hydrolysis step without isolation thereof.

(2) The compounds (II) can also be produced by the following process:

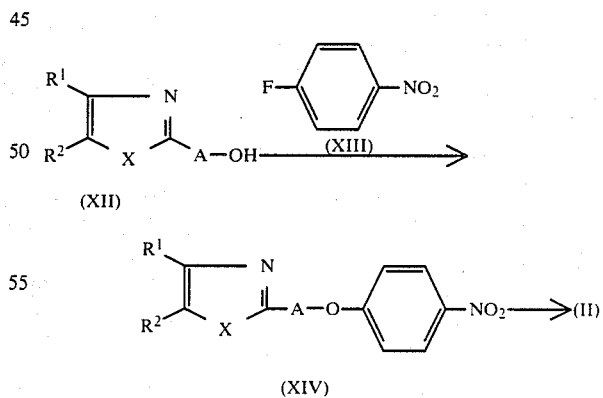

In the formulas, the symbols are as defined above.

In the above process, the compound (XII) is reacted with the compound (XIII) and thereafter, in the same manner as in the case of (VIII) in the process (1) described above, the resulting compound (XIV) is reduced, diazotized and subjected to the Meerwein arylation reaction. Further reaction of the arylation product with thiourea gives (II). The reaction of (XII) with (XIII) can be carried out in a solvent, such as dimethylformamide or tetrahydrofuran, in the presence of, for example, sodium hydride.

Furthermore, the starting compound (IV) required in practicing the present invention can be synthesized by the method described in Chemical & Pharmaceutical Bulletin, vol. 30, p. 3563 (1982).

[EXAMPLES]

Example 1

A mixture of 2-imino-5-{4-[2-(4-methyl-5-phenyl-2-oxazolyl)ethoxy]benzyl}-4-thiazolidinone (5,5 g), ethanol (100 ml) and 2N HCl (60 ml) was heated under reflux for 6 hours and then poured into water and extracted with chloroform. The chloroform layer was washed with water and dried (MgSO$_4$). The solvent was distilled off to give 5-{4-[2-(4-methyl-5-phenyl-2-oxazolyl)ethoxy}-2,4-thiazolidinedione (2.8 g, 50.9%). Recrystallization from ethyl acetate gave colorless prisms. M.p. 168°–169° C.

Elemental analysis: Calcd. for $C_{22}H_{20}N_2O_4S$: C, 64.69; H, 4.93; N, 6.86; Found: C, 64.90; H, 5.05; N, 6.82.

Examples 2–4

In the same manner as Example 1, the compounds listed in Table 1 were obtained.

TABLE 1

| Example No. | R$^1$ | R$^2$ | M.P. (°C.) | Recrystallization solvent | Yield (%) |
|---|---|---|---|---|---|
| 2 | (CH$_3$)$_2$CHCH$_2$— | CH$_3$ | 123–124 | Ethyacetate-hexane | 88.0 |
| 3 | H | CH$_3$ | 156–157 | Ethanol | 71.4 |
| 4 | cyclohexyl (H) | CH$_3$ | 175–176 | Ethanol-dichloromethane | 48.2 |

Example 5

A mixture of 2-imino-5-{4-[2-(5-methyl-4-phenyl-2-oxazolyl)ethoxy]benzyl}-4-thiazolidinone (7.6 g), 1N H$_2$SO$_4$ (70 ml) and dioxane (70 ml) was stirred at 80° C. for 24 hours and then concentrated. The residue was neutralized with potassium carbonate and extracted with ethyl acetate. The ethyl acetate layer was washed with water and dried (MgSO$_4$). The solvent was then distilled off and the oily residue was subjected to column chromatography using silica gel (120 g).

Elution with chloroform-methanol (49:1, v/v) gave 5-{4-[2-(5-methyl-4-phenyl-2-oxazolyl)ethoxy]benzyl}-2,4-thiazolidinedione as an oil (7.06 g, 92.7%).

IR (Neat)cm$^{-1}$: 1755, 1700.

NMR δppm in CDCl$_3$: 2.48(3H, s), 3.02(1H, d, d, J=14 and 9), 3.21(2H, t, J=7), 3.41(1H, d, d, J=14 and 4), 4.35(2H, t, J=7), 4.41(1H, d, d, J=9 and 4), 6.84(2H, d, J=9), 7.11(2H, d, J=9), 7.2~7.75(5H, m), 9.30(1H, broad).

The above-obtained oily substance (7.0 g) was dissolved in methanol (50 ml), and 5N NaOMe (MeOH solution, 3.77 ml) was added to the solution. The mixture was stirred at room temperature for 10 minutes and concentrated and, then, the residue was treated with ether to give sodium salt of 5-{4-[2-(5-methyl-4-phenyl-2-oxazolyl)ethoxy]benzyl}-2,4-thiazolidinedione (5.8 g, 78.6%). Recrystallization from methanol-ether gave colorless prisms. M.p. 261°–262° C. (decomposition).

Elemental analysis: Calcd. for $C_{22}H_{19}N_2O_4SNa$: C, 61.39; H, 4.45; N, 6.51; Found: C, 61.56; H, 4.56; N, 6.64.

Example 6

The procedure of Example 5 was followed to give sodium salt of 5-{4-[2-(5-ethyl-4-phenyl-2-oxazolyl)ethoxy]benzyl}-2,4-thiazolidinedione in 76.9% yield. Recrystallization from ethanol gave colorless prisms. M.p. 248°–250° C. (decomposition).

Elemental analysis: Calcd. for $C_{23}H_{21}N_2O_4SNa$: C, 62.15; H, 4.76; N, 6.30; Found: C, 61.76; H, 4.66; N, 6.40.

Example 7

Sodium hydride (60% in oil, 1.2 g) was added to a solution of 5-(4-hydroxybenzyl)-2,4-thiazolidinedione (3.4 g) in DMF (30 ml), and the mixture was stirred at room temperature for 30 minutes, followed by dropwise addition of a solution of 2-chloromethyl-4-phenyl-thiazole (4.4 g) in DMF (20 ml) at room temperature. The mixture was stirred at room temperature for 1 hour and at 60° C. for 1 hour, poured into water, neutralized with acetic acid and extracted with ethyl acetate. The ethyl acetate layer was washed with water and dried (MgSO$_4$). The solvent was then distilled off and the oily residue was subjected to column chromatography using silica gel (100 g). Elution with benzene-acetone (25:1, v/v) gave 5-[4-(4-phenyl-2-thiazolylmethoxy)benzyl]-2,4-thiazolidinedione (2.9 g, 49.2%). Recrystallization from ethanol gave light-yellow crystals. M.p. 164°–165° C.

Elemental analysis: Calcd. for $C_{20}H_{16}N_2O_3S_2$: C, 60.59; H, 4.07; N, 7.07; Found: C, 60.67; H, 4.03; N, 7.14.

Examples 8–9

The procedure of Example 7 was repeated to give the compounds listed in Table 2.

TABLE 2

| Example No. | X | M.P. (°C.) | Recrystallization solvent | Yield (%) |
|---|---|---|---|---|
| 8 | O | 188–189 | Dichloromethane-methanol | 32.5 |
| 9 | S | 184–185 | Dichloromethane-methanol | 35.3 |

Example 10

Production of tablets

| (a) | (1) Sodium salt of 5-{4-[2-(5-methyl-4- | 30 g |

-continued

| | | |
|---|---|---|
| | phenyl-2-oxazolyl)ethoxy]benzyl}-2,4-thiazolidinedione | |
| (2) | Lactose | 50 g |
| (3) | Corn starch | 15 g |
| (4) | Carboxymethylcellulose calcium | 44 g |
| (5) | Magnesium stearate | 1 g |
| | 1,000 tablets | 140 g |

A mixture of the indicated quantities of (1), (2) and (3), 30 g of (4) and an adequate quantity of water is kneaded, then dried under vacuum, and granulated. The granular composition obtained is mixed with 14 g of (4) and 1 g of (5) and the resulting mixture is tableted on a tableting machine to give 1,000 tablets each containing 30 mg of (1).

Reference Example 1

A mixture of 3-(4-nitrophenoxy)propionic acid (10.5 g), thionyl chloride (11.9 g), N,N-dimethylformamide (0.3 g) and toluene (100 ml) was stirred at 90° C. for 1 hour, then concentrated under reduced pressure, and the oily residue was dissolved in ethyl acetate (30 ml). The solution was added dropwise to a mixture of 3-amino-5-methyl-2-hexanone hydrochloride (8.3 g), sodium carbonate (10.6 g), water (200 ml) and ethyl acetate (100 ml) at room temperature. The mixture was stirred at room temperature for 1 hour and the ethyl acetate layer was separated. The ethyl acetate layer was washed with water and dried (MgSO$_4$). The solvent was distilled off to give 3-[3-(4-nitrophenoxy)propionylamino]-5-methyl-2-hexanone (11.5 g, 71.4%). Recrystallization from ethyl acetate-hexane gave colorless prisms. M.p. 101°–102° C.

Elemental analysis: Calcd. for $C_{16}H_{22}N_2O_5$: C, 59.62; H, 6.88; N, 8.69; Found: C, 59.67; H, 6.79; N, 8.61.

In the same manner as above, there were obtained the compounds listed in Table 3.

TABLE 3

$$NO_2-\text{C}_6H_4-OCH_2CH_2CONHCH(R^1)(COR^2)$$

| R$^1$ | R$^2$ | M.P. (°C.) | Recrystallization solvent | Yield (%) |
|---|---|---|---|---|
| CH$_3$ |  | 134–135 | Ethyl acetate-hexane | 75.5 |
| H | CH$_3$ | 147–148 | Ethanol | 52.6 |
| 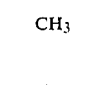 | CH$_3$ | 131–132 | Ethyl acetate | 79.6 |
| 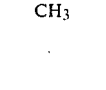 | CH$_3$ | 143–144 | Ethyl acetate-hexane | 63.2 |

TABLE 3-continued $$NO_2-\text{C}_6H_4-OCH_2CH_2CONHCH(R^1)(COR^2)$$

| R$^1$ | R$^2$ | M.P. (°C.) | Recrystallization solvent | Yield (%) |
|---|---|---|---|---|
|  | C$_2$H$_5$ | 132–133 | Ethyl acetate | 76.2 |

Reference Example 2

A mixture of 3-[3-(4-nitrophenoxy)propionylamino]-5-methyl-2-hexanone (11.0 g), phosphorus oxychloride (6.3 g) and toluene (100 ml) was stirred under reflux for 1 hour. After cooling, the mixture was poured into ethyl acetate (200 ml), washed with saturated aqueous sodium hydrogen carbonate and water in that order and dried (MgSO$_4$). The solvent was then distilled off and the oily residue was subjected to column chromatography using silica gel (150 g), whereby 4-isobutyl-5-methyl-2-[2-(4-nitrophenoxy)ethyl]oxazole (8.1 g, 78.6%) was recovered from an ethyl acetate-hexane (1:4, v/v) eluate fraction. Recrystallization from ether-hexane gave colorless needles. M.p. 45°–46° C.

Elemental analysis: Calcd. for $C_{16}H_{20}N_2O_4$: C, 63.14; H, 6.62; N, 9.20; Found: C, 63.14; H, 6.44; N, 9.27.

In the same manner as above, there were obtained the following compounds listed in Table 4.

TABLE 4

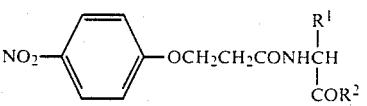

| R$^1$ | R$^2$ | M.P. (°C.) | Recrystallization solvent | Yield (%) |
|---|---|---|---|---|
| CH$_3$ |  | 117–118 | Ethyl acetate-hexane | 89.0 |
| H | CH$_3$ | 89–90 | Ethyl acetate-hexane | 82.3 |
|  | C$_2$H$_5$ | 72–73 | Ether-hexane | 89.5 |
| 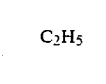 | CH$_3$ | 91–92 | Ether-hexane | 81.7 |
| 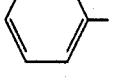 | CH$_3$ | 88–89 | Ether-hexane | 86.3 |

Reference Example 3

A solution of 4-methyl-2-[2-(4-nitrophenoxy)ethyl]-5-phenyloxazole (12.5 g) in methanol (150 ml) was subjected to catalytic reduction in the presence of 5% Pd-C (wet, 3.0 g). The catalyst was then filtered off and the filtrate was concentrated to give 2-[2-(4-aminophenoxy)ethyl]-4-methyl-5-phenyloxazole (11.0 g, 97.3%). Recrsytallization from ethanol gave colorless needles. M.p. 106°–107° C.

Elemental analysis: Calcd. for $C_{18}H_{18}N_2O_2$: C, 73.45; H, 6.16; N, 9.52; Found: C, 73.53; H, 6.11; N, 9.44.

The above procedure was followed to give 2-[2-(4-aminophenoxy)ethyl]-5-ethyl-4-phenyloxazole in 98.7% yield. Recrsytallization from ether-hexane gave colorless prisms. M.p. 89°–90° C.

Elemental analysis: Calcd. for $C_{19}H_{20}N_2O_2$: C, 74.00; H, 6.54; N, 9.08; Found: C, 74.05; H, 6.28; N, 9.25.

Reference Example 4

(1) 2-[2-(4-Aminophenoxy)ethyl]-4-methyl-5-phenyloxazole (10.5 g) was dissolved in acetone (100 ml)-methanol (30 ml), and 47% aqueous HBr (24.6 g) was added to the solution, followed by dropwise addition of a solution of $NaNO_2$ (2.7 g) in water (10 ml) at 5° C. The mixture was stirred at 5° C. for 15 minutes and methyl acrylate (18.4 g) was added thereto. The resulting mixture was then warmed to 38° C. and, with stirring vigorously, cuprous oxide powder (1 g) was added portionwise to the mixture. The mixture was stirred until completion of nitrogen gas generation, then concentrated, and the residue was made basic with aqueous ammonia and extracted with ethyl acetate. The ethyl acetate layer was washed with water and dried ($MgSO_4$). The solvent was distilled off to give crude 2-bromo-3-{4-[2-(4-methyl-5-phenyl-2-oxazolyl)ethoxy]phenyl}propionate as an oil (14.3 g, 89.9%).

IR (Neat)cm$^{-1}$: 1740.

NMR δppm in $CDCl_3$: 2.37(3H, s), 3.0~3.6(2H, m), 3.25(2H, t, J=7), 3.67(3H, s), 4.2~4.5(3H, m), 6.7~7.7(9H, m).

(2) To a solution of the oily substance (14.0 g) obtained in the above procedure (1) in ethanol (150 ml) were added thiourea (2.4 g) and sodium acetate (2.6 g), and the mixture was stirred under reflux for 3 hours and then concentrated. The residue was neutralized with saturated aqueous sodium hydrogen carbonate, followed by addition of ether (50 ml)-hexane (50 ml). The mixture was stirred for 10 minutes and the resulting crystalline precipitate was collected by filtration to give 2-imino-5-{4-[2-(4-methyl-5-phenyl-2-oxazolyl)ethoxy]benzyl}-4-thiazolidinone (6.0 g, 46.2%). Recrystallization from chloroform-methanol gave colorless prisms. M.p. 194°–195° C.

Elemental analysis: Calcd. for $C_{22}H_{21}N_3O_3S$: C, 64.85; H, 5.19; N, 10.31; Found: C, 64.67; H, 5.03; N, 10.02.

In the same manner as above, there was obtained 5-{4-[2-(5-ethyl-4-phenyl-2-oxazolyl)ethoxy]benzyl}-2-imino-4-thiazolidinone. The overall yield from the corresponding amino compound was 39.2%. Recrystallization from methanol gave colorless prisms. M.p. 164°–165° C.

Elemental analysis: Calcd. for $C_{23}H_{23}N_3O_3S$: C, 65.54; H, 5.50; N, 9.97; Found: C, 65.32; H, 5.42; N, 9.95.

Reference Example 5

A solution of 4-isobutyl-5-methyl-2-[2-(4-nitrophenoxy)ethyl]oxazole (7.8 g) in methanol (100 ml) was subjected to catalytic reduction in the presence of 5% Pd-C (wet, 2.0 g). The catalyst was then filtered off and the filtrate was concentrated to give an amino compound as an oil. The amino compound was dissolved in acetone (50 ml)-methanol (20 ml), and 47% aqueous HBr (17.9 g) was added, followed by dropwise addition of a solution of $NaNO_2$ (1.9 g) in water (6 ml) at 5° C. or lower. The mixture was stirred at 5° C. for 15 minutes. Methyl acrylate (15.7 g) was then added and the resulting mixture was warmed to 38° C. and, with stirring vigorously, cupurous oxide powder (0.5 g) was added portionwise to the mixture. The mixture was stirred until completion of nitrogen gas generation and then concentrated. The residue was made basic with aqueous ammonia and extracted with ethyl acetate. The ethyl acetate layer was washed with water and dried ($MgSO_4$). The solvent was distilled off to give crude 2-bromo-3-[4-[2-(4-isobutyl-5-methyl-2-oxazolyl)ethoxy]phenyl]propione as an oil (9.5 g, 86.4%).

IR (Neat)cm$^{-1}$: 1740.

NMR δppm in $CDCl_3$: 0.88(6H, d, J=7), 1.8–2.1(1H, m), 2.17(3H, s), 2.2~2.4(2H, m), 3.0~3.5(2H, m), 3.12(2H, t, J=7), 3.68(3H, s), 4.2–4.5(1H, m), 4.28(2H, t, J=7), 6.7-7.4(4H, m)

(2) To a solution of the oily product (9.2 g) obtained in the above procedure (1) in ethanol (100 ml) were added thiourea (1.7 g) and sodium acetate (1.8 g), and the mixture was stirred under reflux for 3 hours and then concentrated. The residue was neutralized with saturated aqueous sodium hydrogen carbonate, followed by addition of ether (50 ml)-hexane (50 ml). The mixture was stirred for 10 minutes and the resulting crystalline precipitate was collected by filtration and recrystallized from ethyl acetate to give 2-imino-5-{4-[2-(4-isobutyl-5-methyl-2-oxazolyl)ethoxy]benzyl}-4-thiazolidinone (3.0 g, 35.7%) as colorless prisms. M.p. 167°–168° C.

Elemental analysis: Calcd. for $C_{20}H_{25}N_3O_3S$: C, 61.99; H, 6.50; N, 10.84; Found: C, 61.96; H, 6.39; N, 10.70.

In the same manner as above, there were obtained the compounds listed in Table 6. The yield is the overall yield from the corresponding starting amino compound.

TABLE 6

| R¹ | R² | M.P. (°C.) | Recrystallization solvent | Yield (%) |
|---|---|---|---|---|
| H | $CH_3$ | 198–199 | Methanol | 38.6 |
| ⟨H⟩ (cyclohexyl) | $CH_3$ | 152–154 | Ethyl acetate | 50.1 |

TABLE 6-continued

[Structure diagram with R¹, R², N, O, CH₂CH₂O—C₆H₄—CH₂—CH(S)—C(=O)—NH—C(=NH) thiazolidinedione]

| R¹ | R² | M.P. (°C.) | Recrystallization solvent | Yield (%) |
|---|---|---|---|---|
| [phenyl] | CH₃ | 178–180 | Methanol | 47.2 |

Test Example

Blood sugar and lipid lowering activities in mice

The test compound was mixed with a powder diet (CE-2, Clea Japan) at an addition level of 0.005% and the diet was given to KKA$^y$ mice (male, 8–10 weeks old; 5 mice per group) ad libitum for 4 days, during which the mice were freely accessible to water. Blood samples were collected from the orbital venous plexus and assayed for blood sugar level by the glucose oxidase method and for plasma triglyceride (TG) level by enzymaticlly determining glycerol formed using Cleantech TG-S kit (Iatron). Both the activity levels were calculated using the formula given below. The results thus obtained are shown in Table 7. For comparison, data for a known compound of a similar structure are also given.

$$\frac{\left(\begin{array}{c}\text{Level in untreated}\\\text{group}\end{array}\right) - \left(\begin{array}{c}\text{Level in treated}\\\text{group}\end{array}\right)}{(\text{Level in untreated group})} \times 100$$

TABLE 7

| | Blood sugar lowering activity (%) | TG lowering activity (%) |
|---|---|---|
| 1 | 18* | 7 |
| 2 | 53**** | 43*** |
| 4 | 54**** | 51**** |
| 5 | 54**** | 60**** |
| 6 | 46**** | 51**** |
| 7 | 43**** | 42*** |
| 8 | 35** | 24 |
| 9 | 43*** | 43** |
| control compound ciglitazone$^{(1)}$ | 10 | −13 | t-Test
*P < 0.05.
**P < 0.02.
***P < 0.01.
****P < 0.001
$^{(1)}$5-[4-(1-Methylcyclohexylmethoxy)]benzyl-2,4-thiazolidinedione

What is claimed is:

1. A thiazolidinedione derivative of the formula:

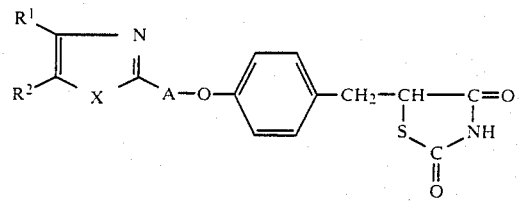

wherein
x is an oxygen atom,
R¹ and R² each independently is
1 hydrogen,
2 saturated aliphatic hydrocarbon residue containing 1 to 8 carbon atoms,
3 saturated alicyclic hydrocarbon residue containing 3 to 7 carbon atoms or unsaturated alicyclic hydrocarbon residue containing 5 to 7 carbon atoms,
4 group resulting from bonding the above mentioned alicyclic hydrocarbon residue to the above-mentioned aliphatic hydrocarbon residue and containing 4 to 9 carbon atoms,
5 phenylalkyl group containing 7 to 9 carbon atoms,
6 naphthylalkyl group containing 11 to 13 carbon atoms,
7 phenyl or
8 naphthyl;
  (i) R¹ and R² each being unsubstituted or substituted by one to three lower alkyl groups containing 1 to 3 carbon atoms when R¹ and R² each is alicyclic hydrocarbon or contains alicyclic hydrocarbon, or
  (ii) R¹ and R² each being unsubstituted or substituted by one to four substituents selected from the group consisting of halogen, hydroxy, cyano, trifluoromethyl, lower alkoxy containing 1 to 4 carbon atoms, lower alkyl containing 1 to 4 carbon atoms and lower alkylthio containing 1 to 3 carbon atoms when R¹ and R² each is phenyl or naphthyl or contains phenyl or naphthyl,
R¹ and R² are combined together to form a saturated or unsaturated divalent chain hydrocarbon residue containing 3 to 5 carbon atoms, which is unsubstituted or substituted by one to four substituents selected from the group consisting of halogen, hydroxy, cyano, trifluoromethyl, lower alkoxy containing 1 to 4 carbon atoms, lower alkyl containing 1 to 4 carbon atoms and lower alkylthio containing 1 to 3 carbon atoms, and
A is a lower alkylene group having 1 to 3 carbon atoms or a salt thereof.

2. The compound as claimed in claim 1, wherein R¹ is a saturated aliphatic hydrocarbon residue containing 1 to 8 carbon atoms, a saturated alicyclic hydrocarbon residue containing 3 to 7 carbon atoms, a phenyl or a naphthyl.

3. The compound as claimed in claim 1, wherein R² is a saturated aliphatic hydrocarbon residue containing 1 to 8 carbon atoms, a phenyl or a naphthyl.

4. The compound as claimed in claim 1, wherein R¹ and R² are combined together to form a saturated or unsaturated divalent chain hydrocarbon residue containing 3 to 5 carbon atoms.

5. The compound as claimed in claim 1, wherein A is methylene.

6. The compound as claimed in claim 1, wherein the compound is 5-{4-[2-(4-isobutyl-5-methyl-2-oxazolyl)ethoxy]benzyl}-2,4-thiazolidinedione.

7. The compound as claimed in claim 1, wherein the compound is 5-{4-[2-(4-cyclohexyl-5-methyl-2-oxazolyl)ethoxy]benzyl}-2,4-thiazolidinedione.

8. The compound as claimed in claim 1, wherein the compound is 5-{4-[2-(5-methyl-4-phenyl-2-oxazolyl)ethoxy]benzyl}-2,4-thiazolidinedione.

9. A pharmaceutical composition suitable for the therapy of a mammal suffering from diabetes and/or hyperlipemia which contains as the effective component a thiazolidinedione derivative of the general formula:

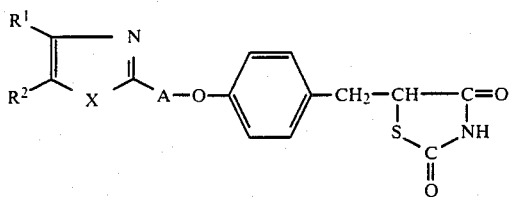

wherein
x is an oxygen or sulfur atom,
$R^1$ and $R^2$ each independently is
1 hydrogen,
2 saturated aliphatic hydrocarbon residue containing 1 to 8 carbon atoms,
3 saturated alicyclic hydrocarbon residue containing 3 to 7 carbon atoms or unsaturated alicyclic hydrocarbon residue containing 5 to 7 carbon atoms,
4 group resulting from bonding the above mentioned alicyclic hydrocarbon residue to the above-mentioned aliphatic hydrocarbon residue and containing 4 to 9 carbon atoms,
5 phenylalkyl group containing 7 to 9 carbon atoms,
6 naphthylalkyl group containing 11 to 13 carbon atoms,
7 phenyl or
8 naphthyl;
  (i) $R^1$ and $R^2$ each being unsubstituted or substituted by one to three lower alkyl groups containing 1 to 3 carbon atoms when $R^1$ and $R^2$ each is alicyclic hydrocarbon or contains alicyclic hydrocarbon, or
  (ii) $R^1$ and $R^2$ each being unsubstituted or substituted by one to four substituents selected from the group consisting of halogen, hydroxy, cyano, trifluoromethyl, lower alkoxy containing 1 to 4 carbon atoms, lower alkyl containing 1 to 4 carbon atoms and lower alkylthio containing 1 to 3 carbon atoms when $R^1$ and $R^2$ each is phenyl or naphthyl or contains phenyl or naphthyl, or
$R^1$ and $R^2$ are combined together to form a saturated or unsaturated divalent chain hydrocarbon residue containing 3 to 5 carbon atoms, which is unsubstituted or substituted by one to four substituents selected from the group consisting of halogen, hydroxy, cyano, trifluoromethyl, lower alkoxy containing 1 to 4 carbon atoms, lower alkyl containing 1 to 4 carbon atoms and lower alkylthio containing 1 to 3 carbon atoms, and
A is a lower alkylene group having 1 to 3 carbon atoms or a pharmacologically acceptable salt thereof.

* * * * *